United States Patent [19]

Camerman

[11] 4,001,342
[45] Jan. 4, 1977

[54] PRODUCTION OF ETHYLPHENOLS

[75] Inventor: Philippe Jean Andre Camerman, Wezembeek-Oppem, Belgium

[73] Assignee: Labofina S. A., Brussels, Belgium

[22] Filed: Feb. 10, 1975

[21] Appl. No.: 548,446

[30] Foreign Application Priority Data

Feb. 19, 1974 United Kingdom .............. 7550/74

[52] U.S. Cl. ...................... 260/624 R; 260/601 R; 260/618 R; 260/667; 260/592; 260/610 B
[51] Int. Cl.² ........................................ C07C 39/06
[58] Field of Search ....... 260/621 C, 610 B, 624 R, 260/624 C, 601 R, 667

[56] References Cited

UNITED STATES PATENTS

| | | | |
|---|---|---|---|
| 2,671,809 | 3/1954 | Fortuin et al. ................. | 260/621 C |
| 3,187,052 | 6/1965 | Nelson ........................... | 260/621 C |
| 3,436,429 | 4/1969 | Flickinger et al. ............. | 260/621 G |
| 3,497,561 | 2/1970 | Gelbein ......................... | 260/624 C |

*Primary Examiner*—James O. Thomas, Jr.
*Assistant Examiner*—W. B. Lone

[57] ABSTRACT

A process for the production of ethylphenol comprising the oxidation of diethylbenzene into diethylbenzene monohydroperoxide, withdrawing the reaction mixture, separating the unconverted diethylbenzene therefrom to obtain a hydroperoxide concentrate containing at least 40% of diethylbenzene monohydroperoxide, mixing said concentrate with a solvent selected from the group consisting of the lower molecular weight aliphatic alcohols and ketones, decomposing said hydroperoxide by intimate contact with a strong acid, hydrogenating the decomposition mixture and recovering ethylphenol from the hydrogenated mixture.

5 Claims, No Drawings

PRODUCTION OF ETHYLPHENOLS

BACKGROUND OF THE INVENTION

This invention relates to a process for producing ethylphenols via the liquid phase oxidation of diethylbenzenes.

In British Patent application No. 39002/73, a process is described which comprises oxidation of diethylbenzene by passing a molecular oxygen containing gas into contact with said diethylbenzene at a temperature between 100° and 180° C to thereby convert 5 to 30% of said diethylbenzene into diethylbenzene hydroperoxide, withdrawing the reaction mixture, separating the unconverted diethylbenzene therefrom to obtain a hydroperoxide concentrate containing at least 40% of diethylbenzene hydroperoxide, mixing the diethylbenzene hydroperoxide concentrate with a solvent, such as a low molecular weight aliphatic alcohol or ketone, decomposing said hydroperoxide by intimate contact with a strong acid and then neutralizing the resulting mixture, distilling the neutralized mixture to recover a bottom fraction containing ethylphenol and a top fraction containing acetaldehyde.

The process may be summarized by the following reactions:

oxidation of diethylbenzene into diethylbenzene hydroperoxide

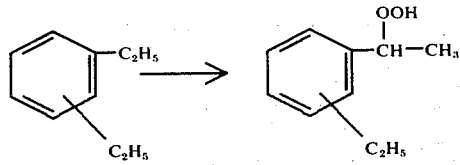

and decomposition of said hydroperoxide into ethylphenol and acetaldehyde

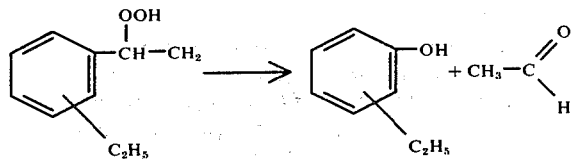

Some by-products are formed during said process and they have a detrimental effect not only on the selectivity of the total reaction but also on the recovery and the purification of ethylphenol.

It is an object of the present invention to provide an improved process for the production of ethylphenol.

A further object of the present invention is to increase the yield of ethylphenol calculated on the amount of converted diethylbenzene.

Another object of the present invention is to provide a simplified process for the manufacture of ethylphenol from diethylbenzene, said ethylphenol being recovered by distilling a mixture containing a lower number of by-products.

A remaining object of the present invention is to provide a process for the production of ethylphenol.

SUMMARY OF THE INVENTION

The process of the present invention comprises the steps of oxidizing diethylbenzene into diethylbenzene monohydroperoxide, withdrawing the reaction mixture, separating a major part of the unconverted diethylbenzene therefrom to obtain a hydroperoxide concentrate containing at least 40% of diethylbenzene monohydroperoxide, mixing said concentrate with a solvent selected from the low molecular weight aliphatic alcohols and ketones, decomposing said hydroperoxide by intimate contact with a strong acid, hydrogenating the decomposition mixture, and recovering ethylphenol from the hydrogenated mixture.

It has been found that by hydrogenating the decomposition mixture, the by-products formed during the oxidation step and the decomposition step are converted either into diethylbenzene or into ethylphenol. Some of these by-products are formed during the oxidation step and they comprise nonperoxidic compounds and peroxidic compounds, having the general formula

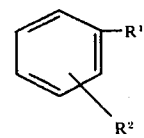

wherein $R^1$ and $R^2$ are respectively

| $R^1$ | $R^2$ | By-product |
|---|---|---|
| $-C\!\!\stackrel{O}{\underset{}{\diagdown}}\!\!CH_3$ | $-C_2H_5$ | ethylacetophenone |
| $-CH(OH)-CH_3$ | $-C_2H_5$ | 1-(ethylphenyl)ethanol |
| $-C\!\!\stackrel{O}{\underset{}{\diagdown}}\!\!CH_3$ | $-C\!\!\stackrel{O}{\underset{}{\diagdown}}\!\!CH_3$ | diacetylbenzene |
| $-C\!\!\stackrel{O}{\underset{}{\diagdown}}\!\!CH_3$ | $-CH(OH)-CH_3$ | 1-(acetylphenyl)ethanol |
| $-CH(OH)-CH_3$ | $-CH(OH)-CH_3$ | bis(1-hydroxyethyl)benzene |
| $-CH(OOH)-CH_3$ | $-C\!\!\stackrel{O}{\underset{}{\diagdown}}\!\!CH_3$ | 1(acetylphenyl)ethylhydroperoxide |
| $-CH(OOH)-CH_3$ | $-CH(OOH)-CH_3$ | bis(1-hydroperoxyethyl)benzene |

Some by-products are also formed during the decomposition reaction. They consist particularly of ethylacetophenone and 1(ethylphenyl)ethanol, which are probably formed together with ethylphenol when diethylbenzene monohydroperoxide is decomposed by the strong acid, and of acetylphenol which is formed from 1(acetylphenyl)ethylhydroperoxide.

By hydrogenating the decomposition mixture, the acetyl groups

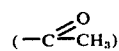

are converted into alcohol groups (—CHOH-CH₃) and then into ethyl groups (—C₂H₅). The above by-products are consequently hydrogenated into either diethylbenzene, which can be recycled, or into ethylphenol. The ethylphenol yield based on converted diethylbenzene is thus increased by the process of the present invention.

It was unexpected that the above specified undesirable by-products could be hydrogenated into valuable products. Indeed, in the production of phenol and acetone via the liquid phase oxidation of cumene and decomposition of cumene peroxide, some by-products such as methylphenylcarbinol, acetophenone and alpha-methylstyrene are also formed. By hydrogenating the reaction mixture containing phenol, acetone and these by-products, only alpha-methylstyrene is hydrogenated into cumene (U.S. Pat. No. 3,436,429).

DESCRIPTION OF THE PREFERRED EMBODIMENTS

The hydrogenation step according to the present invention may be applied directly to the acidic reaction mixture obtained after decomposition of the diethylbenzene monohydroperoxide concentrate, or after removal of acetaldehyde from this acidic reaction mixture, or after neutralization of this reaction mixture and removal of the solvent and/or of acetaldehyde.

The reaction conditions (type and amount of catalyst, temperature, pressure) during the hydrogenation step must be selected so that the acetyl and alcohol groups are hydrogenated into ethyl groups, but without hydrogenation of the benzene nucleus, without hydrogenolysis of the phenolic hydroxyl group and without hydrogenation of acetaldehyde and of the solvent mixed with the monohydroperoxide concentrate.

In one embodiment of this invention, the hydrogenation step is applied to the acidic decomposition mixture containing the acetaldehyde and the solvent. In this embodiment hydrogenation takes place with palladium as the catalyst, optionally on a carrier such as alumina or active carbon.

In another embodiment of this invention, the decomposition mixture, after having been neutralized or not, is distilled to remove the acetaldehyde and the solvent. More particularly is this embodiment followed when the solvent is a ketone. The resulting mixture is then hydrogenated. Suitable catalysts are based on transition metals of Groups VI and VII, optionally on a carrier, and particularly palladium, cobalt alloys, nickel, and its alloys, platinum and its alloys, copper chromite and similar hydrogenation catalysts. The catalyst activity and especially the hydrogenolysis activity may be promoted by usual activators, for example, acids for palladium catalysts.

The hydrogenation step is preferably carried out at a temperature within the range of about 10° to 150° C and under a pressure which may be varied widely but which is generally between about 0.1 to 300 atmospheres.

The invention will now be further described by reference to the following example.

EXAMPLE 1

Redistilled meta-diethylbenzene was charged to a glass-reactor equipped with a stirring device, a cooling system and a Dean and Stark condenser. Air was bubbled into the liquid with agitation and the reaction mass then was heated to 150° C, at which temperature oxygen uptake began rapidly. The percentage of oxygen in the vent gas was then depressed to about 9 to 10% and remained at this value throughout the course of the reaction. The temperature was progressively decreased as the diethylbenzene conversion increased in such a way that 140° C was reached when about 20% conversion was obtained as determined by oxygen absorption measurements. The reaction mixture was then rapidly cooled to 30° – 40° C and collected.

The hydroperoxides so obtained were concentrated by distilling off most of the unconverted diethylbenzene at 50° C and under 2 mm. Hg. One hundred (100) grams of the hydroperoxides concentrate contained:

| | |
|---|---|
| diethylbenzene | 17.1 g. |
| ethylacetophenone | 6.9 g. |
| 1(ethylphenyl)ethanol | 1.3 g. |
| diacetylbenzene + 1(acetylphenyl)ethanol + bis(1-hydroxyethyl)benzene | 0.5 g. |
| 1(ethylphenyl)ethylhydroperoxide | 69.4 g. |
| 1(acetylphenyl)ethylhydroperoxide | 1.0 g. |
| bis(1-hydroperoxyethyl)benzene | 3.3 g. |
| acids and non-identified products | 0.5 g. |

This composition shows that the yield of diethylbenzene monohydroperoxide or 1(ethylphenyl) ethylhydroperoxide was 83.3% and the amount of non-Peroxidic by-products formed from diethylbenzene was 12.3%, based on the converted diethylbenzene.

Two hundred (200) grams of this mixture were introduced during a 15 minute peroid into 700 ml. of boiling acetone containing 2 g. of 98% $H_2SO_4$. The resulting mixture was maintained at 60° during 20 minutes. A part of the formed acetaldehyde and a part of the solvent were distilled off.

After cooling to about 20° C, the mixture was divided in two equal parts.

The analysis of one of these parts has shown that 99% of the hydroperoxides have been converted. Said part contained:

| | |
|---|---|
| diethylbenzene | 17 g. |
| ethylacetophenone | 9.2 g. |
| 1(ethylphenyl)ethanol | 3.2 g. |
| diacetylbenzene + 1(acetylphenyl)ethanol + bis(1-hydroxyethyl)benzene | 1.9 g. |
| ethylphenol | 46.8 g. |

The yield of ethylphenol calculated on converted ethylphenyl monohydroperoxide was thus 91.7% and the yield of ethylphenol calculated on the initially converted diethylbenzene was 76.4%.

A palladium on active carbon (catalyst containing 5% of palladium) in the amount of 1.5 grams were added to the other part of the mixture and introduced into an autoclave. Hydrogenation was carried out at 10 atm., the reaction mixture being heated from 20° to 60° C during a 40 minute period and maintained at 60° C until no more hydrogen was absorbed.

The pressure was then released and the reaction mixture cooled and collected. The analysis showed that said reaction mixture was free from ethylacetophenone, 1-(ethylphenyl) ethanol, diacetylbenzene, 1(acetylphenyl)ethanol and bis(1-hydroxyethyl)benzene. The reaction mixture contained 29.5 g. of diethylbenzene and 46.0 g. of ethylphenol, which are easily separated by distillation at atmospheric pressure. The increase of the amount of diethylbenzene results from the hydrogenation of aromatic detones and alcohols into diethylbenzene.

The yield of ethylphenol calculated on the diethylbenzene which has actually been converted into oxygenated derivatives (or in fact into hydroperoxides) is 92 mole %.

This example shows that the separation and the purification of the ethylphenol is simplified when the reaction mixture resulting from the decomposition of the hydroperoxides is hydrogenated.

EXAMPLE 2

The procedure described in Example 1 was repeated for producing a concentrate of hydroperoxide which was treated by sulfuric acid in the presence of acetone. The mixture resulting from the decomposition of this concentrate was neutralized by an aqueous solution of NaOH and then heated to 60° C in order to remove the acetone and the acetaldehyde. The salts and tarry materials were removed by a flash distillation of the mixture at 140° C at under 5 mm. Hg. The mixture (347 g) (Mixture A) was obtained and it contained diethylbenzene, 56.2 g (or 16.2% by weight); ethylphenol, 160.0 g (46.1%) ethylacetophenone, 72.5 g (20.9%); 1(ethylphenyl)ethanol, 30.5 g (8.8%); and others, 27.8 g (8%). This mixture was introduced into a stainless steel autoclave containing 30 g of nickel on activated granulated kieselguhr (catalyst containing 55% by weight of nickel) and was treated by hydrogen at 130° C and under 15 kg/cm2. When about 1 mole of $H_2$ was absorbed, the catalyst was removed. The mixture (Mixture B) contained diethylbenzene, 124 g; ethylphenol, 150 g; ethylacetophenone, 1.6 g; 1(ethylphenyl) ethanol, 23.2 g; and ethylcyclohexanol. 5.4 g. This example shows that 75% of ethylacetophenone plus 1(ethylphenyl) ethanol was hydrogenated with formation of diethylbenzene. The yield of ethylphenol based on diethylbenzene used is increased.

EXAMPLE 3

Mixture A of Example 2 was divided into three equal parts. These parts were hydrogenated at 150° C and under a pressure of 30 kg/cm2, respectively with the following catalysts:

palladium on $Al_2O_3$ (catalyst containing 0.5% of Pd)
copper chromite
nickel-cobalt alloy (95 Ni-5 Co) on $Al_2O_3$ (catalyst containing 5% by weight of alloy).

The analysis of the hydrogenated mixtures showed that each of them had a composition similar with the composition of Mixture B of Example 2.

What is claimed is:

1. In a process for the production of ethylphenol comprising the steps of (1) oxidizing diethylbenzene by passing a molecular oxygen containing gas into contact with said diethylbenzene at a temperature between 100° C. and 180° C. to convert 5% to 30% of diethylbenzene into diethylbenzene mono-hydroperoxide, (2) withdrawing the reaction mixture, (3) separating the unconverted diethylbenzene therefrom to obtain a mono-hydroperoxide concentrate containing at least 40% of diethylbenzene mono-hydroperoxide, (4) mixing the diethylbenzene mono-hydroperoxide concentrate with a solvent selected from the group consisting of lower alkanols, lower alkanones and mixtures thereof, (5) decomposing said monohydroperoxide by intimately contacting said mixture of diethylbenzene mono-hydroperoxide and solvent with a strong acid, whereby there is produced a decomposition mixture containing as by-products ethylacetophenone, 1-(ethylphenyl) ethanol, diacetylbenzene, 1-(acetylphenyl)ethanol, bis(1-hydroxyethyl) benzene, 1(acetylphenyl)ethylhydroperoxide, and bis(1-hydroperoxyethyl)benzene, and (6) recovering from the decomposition mixture a bottom fraction containing ethyl phenol and a top fraction containing acetaldehyde, wherein the improvement comprises the step of hydrogenating said decomposition mixture at a temperature within the range of from about 10° to 150° C., at a pressure within the range of 0.1 to 300 atmospheres and in the presence of a hydrogenation catalyst containing a transition metal of Groups VI and VII of the Periodic Table, whereby said by-products are converted into diethyl benzene or ethylphenol, without hydrogenation of the benzene nucleus, without hydrogenolysis of the phenolic hydroxyl group and without hydrogenation of any acetaldehyde or solvent which may be present, whereby the yield of ethylphenol based upon converted diethylbenzene is increased.

2. The process of claim 1 in which said hydrogenation is carried out before said step of recovering and in the presence of a palladium catalyst.

3. The process of claim 2 wherein said palladium catalyst comprises palladium dispersed on a carrier selected from the group consisting of alumina and active carbon.

4. The process of claim 1 wherein said solvent in a lower alkanone.

5. The process of claim 4 wherein said hydrogenation is carried out subsequent to said step of recovering and in the presence of a catalyst selected from the group consisting of palladium, nickel, platinum, and alloys thereof, and copper chromite.

* * * * *